United States Patent [19]

Goodale et al.

[11] Patent Number: 5,356,525
[45] Date of Patent: Oct. 18, 1994

[54] SAMPLE HANDLING SYSTEM

[75] Inventors: David L. Goodale, Yorba Linda; Steven D. Mack, Mira Lona, both of Calif.

[73] Assignee: Beckman Instruments, Inc., Fullerton, Calif.

[21] Appl. No.: 72,202

[22] Filed: Jun. 3, 1993

Related U.S. Application Data

[63] Continuation of Ser. No. 48,708, Apr. 16, 1993, abandoned.

[51] Int. Cl.⁵ .................. G01N 27/26; G01N 27/447; G01N 35/00
[52] U.S. Cl. .............................. 204/299 R; 204/180.1; 436/43
[58] Field of Search ................ 204/180.1, 299 R; 436/43

[56] References Cited

U.S. PATENT DOCUMENTS

| | | | |
|---|---|---|---|
| 4,287,155 | 9/1981 | Tersteeg et al. | 422/64 |
| 4,325,909 | 4/1982 | Coulter et al. | 422/63 |
| 4,629,703 | 12/1986 | Uffenheimer | 422/63 X |
| 4,632,808 | 12/1986 | Yamamoto et al. | 422/63 X |
| 4,695,430 | 9/1987 | Coville et al. | 422/65 |
| 4,774,055 | 9/1988 | Wakatake et al. | 422/63 X |
| 4,788,150 | 11/1988 | Nelson et al. | 436/45 |
| 4,900,513 | 2/1990 | Barker et al. | 422/64 |
| 4,908,320 | 3/1990 | Zakowski et al. | 436/45 |
| 5,008,081 | 4/1991 | Blau et al. | 436/43 X |
| 5,045,172 | 9/1991 | Guzman et al. | 204/299 R |
| 5,051,238 | 9/1991 | Umetsu et al. | 422/64 |
| 5,102,623 | 4/1992 | Yamamoto et al. | 422/63 |
| 5,122,342 | 6/1992 | McCulloch et al. | 422/65 |
| 5,164,318 | 11/1992 | Sato et al. | 422/64 |
| 5,167,926 | 12/1992 | Kimura et al. | 422/67 |

FOREIGN PATENT DOCUMENTS

0339779A2  3/1989  European Pat. Off.

*Primary Examiner*—John Niebling
*Assistant Examiner*—John S. Starsiak, Jr.
*Attorney, Agent, or Firm*—William H. May; Arnold Grant; Gary T. Hampson

[57] ABSTRACT

A sample handling system suitable for use with a sample segment and a plurality of capillaries, including a rotatable and vertically translatable arm including an attachment portion to removably receive and retain the sample segment and a manifold adapted to removably retain the sample segment and the plurality of capillaries. The sample segment may be held by the attachment portion by the application of vacuum. Rotatable and vertical translation of the arm may be accomplished by a spindle and guide rails that are resiliently retained. The manifold may include a degassing reservoir and fluid manipulating valves retained by adapters configured to fail if external force is applied to the associated valve.

43 Claims, 12 Drawing Sheets

SAMPLE HANDLING SYSTEM

RELATED APPLICATIONS

This application is a continuation of U.S. patent application Ser. No. 08/048,708, filed Apr. 16, 1993 now abandoned.

The present application is related to the following applications that are commonly assigned and filed concurrently herewith, and which are incorporated herein by reference:

U.S. patent application Ser. No. 08/071,831, entitled "Sample Segment", filed in the names of Ronald C. Glenday, David L. Goodale, and Steven D. Mack, which is a continuation of U.S. patent application Ser. No. 08/048,716, filed Apr. 16, 1993 now abandoned; and U.S. patent application Ser. No. 08/071,832, entitled "Capillary and Capillary Retaining System", filed in the names of David L. Goodale and George I. Reeves, which is a continuation of U.S. patent application Ser. No. 08/048,709, filed Apr. 16, 1993 now abandoned.

FIELD

The present invention relates generally to the field of electrophoresis and more particularly to capillary electrophoresis, and still more particularly to a sample handling system suitable for use in an automated capillary electrophoresis analyzer. The invention may be used in, but is not limited to, clinical chemistry.

BACKGROUND

The value of capillary electrophoresis as a separation and analytical technique has been recognized for some time. In capillary electrophoresis, a small tube or capillary is filled with an electrically conductive fluid, or buffer. A small quantity of a sample to be analyzed is introduced into one end of the capillary bore, the ends of the capillary are placed into separate reservoirs of buffer, and a direct current high voltage is applied to the ends of the capillary by means of electrodes positioned in the buffer reservoirs, causing a small current to flow through the capillary.

With the correct polarity applied across the capillary, the sample begins to migrate toward the other end of the capillary and the buffer begins to migrate the opposite direction. As this migration occurs, different molecules in the sample travel at different rates, causing the sample to become separated into bands of these different molecules. These bands or groups of different molecules are detected near the other end of the capillary by, for example, passing a perpendicular light beam through the bore of the capillary. Changes to the light beam, such as absorbance caused by the different molecules, are detected as the separated molecules pass through the beam, thus identifying the different molecules or the classes or categories of molecules in the sample and the relative concentration of such molecules.

To make the technique easier to use and less labor intensive, several efforts have been made to automate the analysis of samples in capillary electrophoresis systems. For example European Patent Application number 89302489.3, publication number 0,339,779 A2, corresponding to U.S. patent application Ser. No. 188,773, filed Apr. 29, 1988 now abandoned (Burolla) describes an automated capillary electrophoresis apparatus. That apparatus includes two conveyors for positioning vials under ends of a capillary mounted in a cartridge. The ends of the capillaries along with electrodes are inserted into the vials by means of hypodermics that pierce caps on the vials. A single detector provides detection of the electrophoresed sample.

Automated capillary electrophoresis apparatus is described in U.S. Pat. No. 5,045,172 to Guzman. The Guzman apparatus includes two rotating tables at opposite ends of the apparatus that hold sample and buffer cups. A capillary, which is described in Guzman as being a single capillary or a plurality of capillary tubes operated in parallel or in a bundle, has two opposite ends. These ends are positioned by automated arms and posts in respective corresponding pairs of cups to first draw sample into the capillary and to then electrophorese the sample. As with Burolla, a single detector is used to detect the results.

Both of these automated analyzers just described, however, present drawbacks with respect to sample handling. For example, each of such analyzers requires considerable manual manipulation despite their automated nature, such as preparing and placing individual sample and buffer vials onto the analyzer, programming the analyzer for the various analytical routines, and the like. Because only one sample can be electrophoresed and detected during each analysis cycle of the analyzers, the number of samples per unit timer or throughput, is severely restricted as compared to the needs of, for example, most routine clinical laboratory work.

A characteristic of prior art automated analyzers is that such analyzers often use multiple automated pipettes and turntables to move samples from a sample input area through the automated analysis cycle. Such an analyzer, for example, is disclosed in U.S. Pat. No. 4,908,320. Although such analyzers can achieve considerable throughput, the analyzers can be expensive and are often relatively large, floor-standing units.

Thus, there is a need for a sample handling system suitable for use, for example, in an automated capillary electrophoresis analyzer, that increases potential throughput of the analyzer yet is easy and relatively inexpensive to maintain. There is also a need for such a system that enables the analyzer to be relatively compact with few automated handling devices that can otherwise increase cost and size.

SUMMARY OF THE INVENTION

The present invention is directed to a sample handling system and aspects of such a sample handling system that can increase capillary system throughput, yet is relatively inexpensive to manufacture and easy to maintain. The system is preferably highly automated, providing sample pipetting, diluting and additional reagent handling in a relatively small volume or instrument "footprint".

A capillary electrophoresis sample handling system in accordance with the present invention may be suitable for use, for example, with a sample segment and a plurality of capillaries. Such a system may include an arm including receiving means for receiving and removably retaining the sample segment. Rotational means is provided for moving the arm about a central rotational axis and translational means is provided for moving the arm along a translational axis, the translational axis passing through the rotational axis. The system may also include manifold means for removably receiving the sample segment and the plurality of capillaries. The rotational means allows other actions to be performed while electrophoresing is being done, thereby increasing throughput. Also, the rotational means can be compact, allowing an analyzer in which the invention is used to be likewise compact, such as a bench-top unit.

To retain the sample segment on the arm, the system may include a port in the receiving means and means for controllably applying vacuum to the port to thereby removably retain the sample segment by the receiving means.

The rotational means may include a spindle and bearing means for rotatably retaining the spindle by a frame, with the bearing means including a rotational bearing and a resilient member between the rotational bearing and the frame. The resilient member may take the form of an o-ring.

Additionally, the translational means may include parallel guide rails having first and second ends, a carriage guided by the guide rails and which carries the arm, motive means for moving the carriage along the guide rails, and means for flexibly mounting the guide rails at the first end thereof. The motive means may include a lead screw having first and second ends proximate the first and second ends of the guide rails. In such an embodiment, the carriage includes a threaded portion engaged with the lead screw, and the motive means further includes motor means for driving the lead screw. The motor means may additionally include flexible coupling means connecting the motor means to the lead screw, to thereby provide flexibility between the guide rails and lead screw to prevent binding and alignment problems that might otherwise arise.

The resilient member and the flexible mounting for the guide rails also provide vibration and noise damping, decreasing the noise of the system and reducing vibration that might otherwise be transmitted throughout the analyzer in which the system resides and to a bench or other support for such an analyzer.

The system may also include a pipette probe that has a tip. The manifold may include a wash cell for the probe tip and the system may also include means for supporting the pipette probe such that the tip is in the wash cell.

Liquid level sensing means for sensing contact between the probe tip and liquid may further be included in the system. The manifold means may include a first conduit and means for receiving an end of capillaries in the conduit, a second conduit providing fluid communication between the first conduit and the wash cell, and valve means for controllably flowing liquid into the first conduit, the relative elevation of the first conduit and the wash cell being such that liquid flows into the wash cell via the second conduit and is detected by the level sensing means when the first conduit is full of liquid. In this fashion, the level sensing is useful not only for detecting wash level within the wash cell, but also for detecting that the first conduit if filled with liquid in preparation for sample electrophoresing.

The manifold means may include a sample segment receiving station and an optical detection station. The sample segment receiving station may include means for removably retaining a sample segment and means for removably retaining first ends of the capillaries within wells of the sample segments. The optical detection station may include means for receiving and retaining second ends of the capillaries within the conduit.

The manifold means may also include an internal chamber having dimensions particularly suited for liquid degassing, as well as valves for directing liquid into and out of the internal chamber and for applying a degassing vacuum to the internal chamber.

It is also contemplated according to the present invention that the arm, translational means, rotational means, and the manifold means are individually inventive as are various combinations of such elements and attributes of such elements.

BRIEF DESCRIPTION OF THE DRAWINGS

These and other features, aspects, and advantages of the present invention will become better understood with reference to the following description, appended claims, and accompanying drawings where:

DETAILED DESCRIPTION

Figure 1:
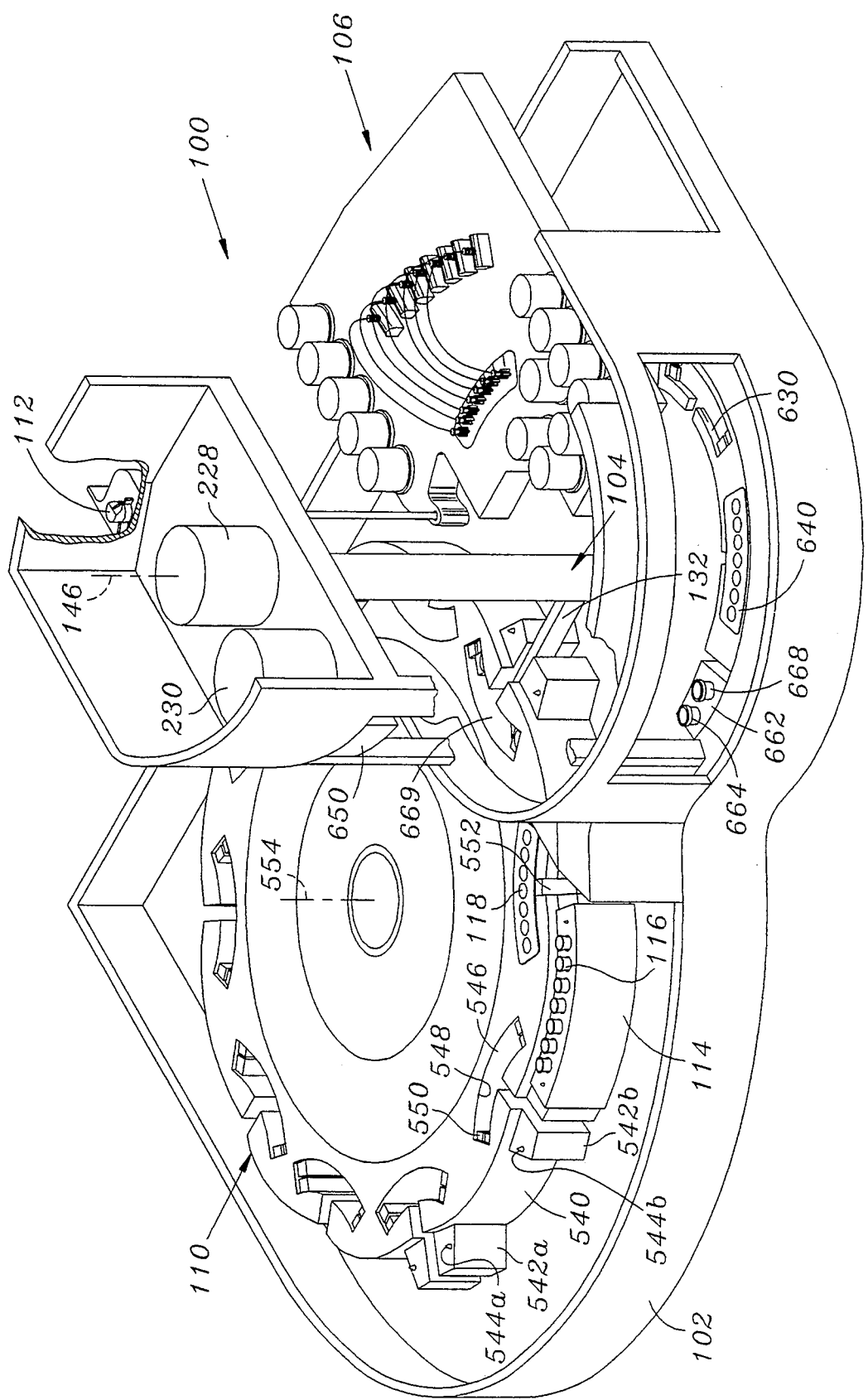
FIG. 1 is a perspective view of a sample handling system in accordance with the present invention.

With respect to FIG. 1, a sample handling system 100 in accordance with the present invention may be useful in, for example, an automated capillary electrophoresis analyzer, a frame 102 of which is partially shown in FIG. 1. Such an analyzer may also include fluid and computer control systems for automated operation. Preferably, such an analyzer may include a plurality of capillaries as is disclosed, for example, in U.S. patent application Ser. No. 07/916,308, filed Jul. 17, 1992 and entitled *Multi-Channel Capillary Electrophoresis System*, and which is incorporated herein by reference.

With continued reference to FIG. 1, the sample handling system 100 includes a transport assembly 104 and a manifold 106, and may also include a sample wheel 110 and a pipette probe 112. The sample wheel 110 is adapted to support sectors 114 that in turn carry test tubes 116 holding samples to be analyzed. The sample wheel 110 also is adapted to support one or more sample segments 118.

Figure 2:
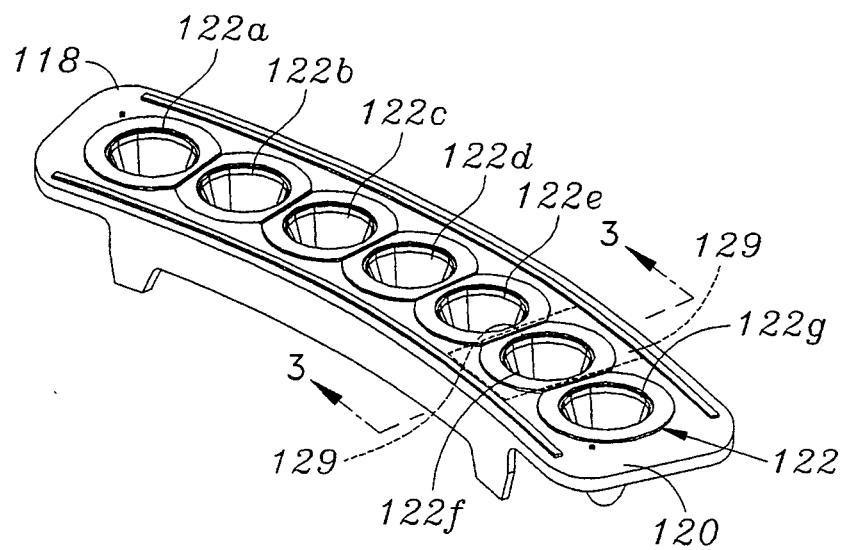
FIG. 2 is a perspective view of a sample segment that may be used with the present invention.
Figure 3:
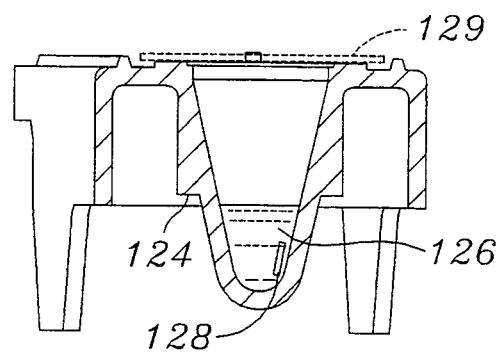
FIG. 3 is a section view of the sample segment of FIG. 2 taken along line 3—3 thereof.
Figure 4:
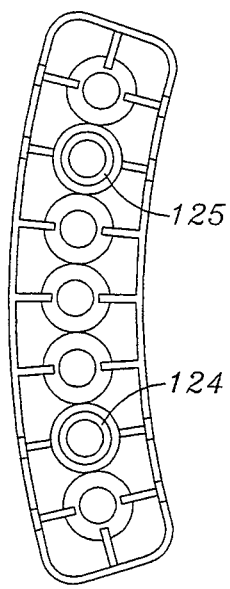
FIG. 4 is a bottom view of the sample segment of FIG. 2.

The sample segment 118 includes a generally arcuate body 120 (FIGS. 2–4) defining a plurality of wells 122. The sample segment 118 may include seven wells 122a–122g, although a larger or smaller number of wells 122 may also be used. The external surfaces of two of the wells 122 define flat annular surfaces 124, 125. In the embodiment of FIG. 2, the surfaces 124, 125 are formed about the exterior of the second of the wells 122b, 122f from the outer ends of the sample segment 118. Selected ones of the wells 122 may include a reagent 126 and a mixing element 128, the mixing element 128 taking the form of 0.040 inch diameter nickel chromium wire about 0.125 inch long. The wells 122 including reagent 126 may be closed by means of a cover or label 129 which may be a laminate of foil and plastic film and which is partially shown in phantom in FIG. 2.

The transport assembly 104 (FIG. 1) transports the sample segment 118 from the sample wheel 110 to the manifold 106 for analysis of samples contained within the sample segment 118 and to other intermediate locations. The transport assembly 104 also transports the pipette probe 112 for various pipetting and diluting operations (as described more fully hereinbelow).

Figure 5:
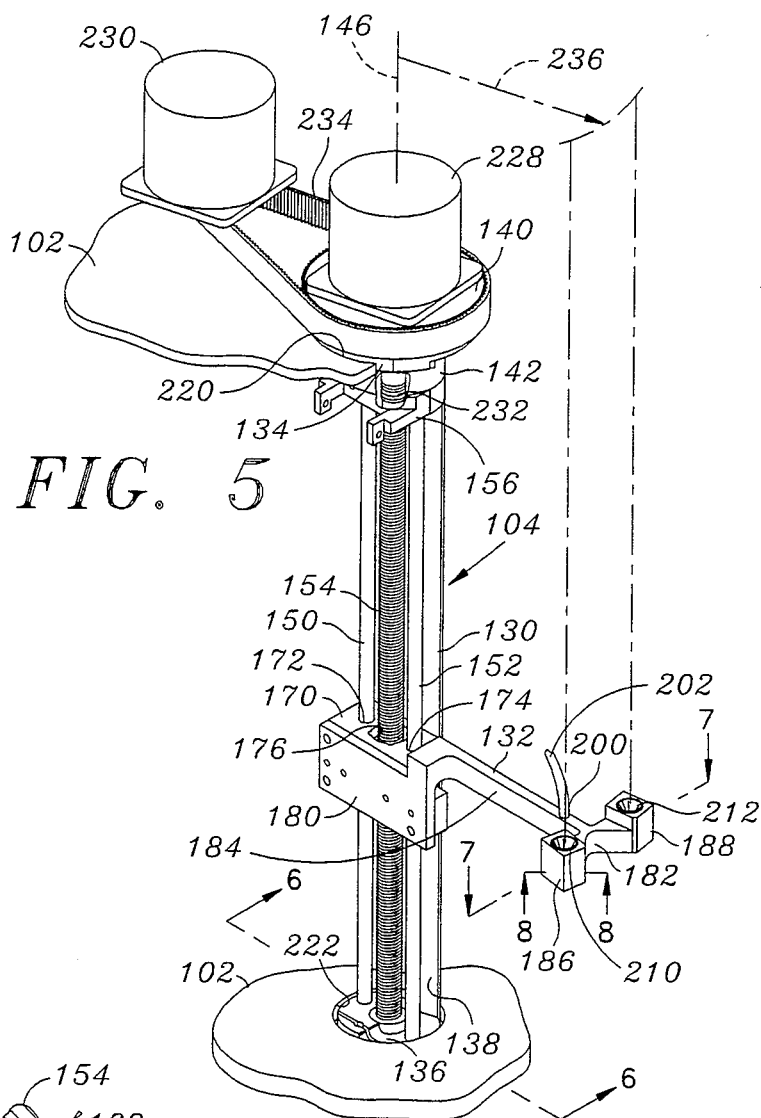
FIG. 5 is a perspective view of a transport assembly of the sample handling system of FIG. 1.
Figure 6:
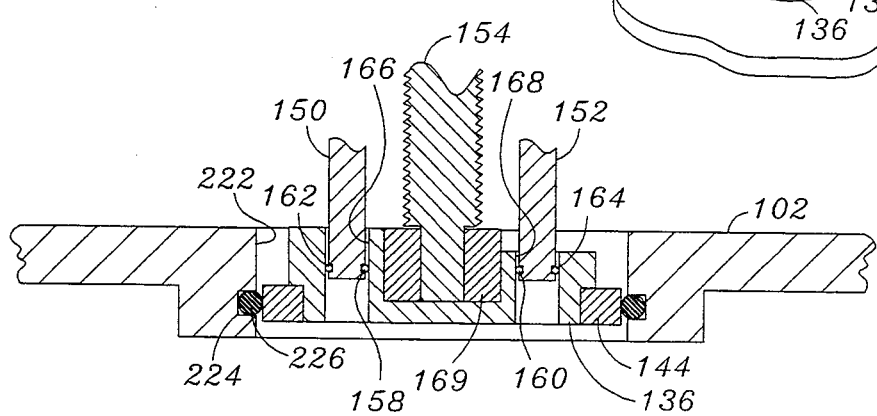
FIG. 6 is a section view of the transport assembly of FIG. 5 taken along 6—6 thereof.

With reference to FIGS. 5 and 6, the transport assembly 104 includes a rotational means or a spindle 130, and an arm 132. The spindle 130 includes an upper support portion 134 (as viewed in FIG. 5), a lower support portion 136, and a rail 138 between the upper and lower support portions 134, 136. The upper support portion is formed to define a gear 140 and a bearing 142 is fixed to the upper support portion 134 immediately below the gear 140. The lower support portion 136 is similarly fixed to a bearing 144, the bearings 142, 144 and gear 140 being axially aligned with a rotational or central axis 146 of the spindle 130 to provide rotation of the spindle 130 about the central axis 146.

The spindle 130 carries at least one guide shaft and in the specific embodiment disclosed herein, has two guide shafts 150, 152 and a threaded lead screw 154. The guide shafts 150, 152 are fixed to the upper support portion 134 by a clamp 156. The lower ends of the guide shafts 150, 152 define circumferential grooves 158, 160, respectively, which receive corresponding resilient o-rings 162,164, respectively. To support the lower ends of the guide shafts, the o-rings 162, 164 are compressed and fitted into receiving openings 166, 168 formed into the lower support portion 136, the openings 166, 168 supporting the o-rings 162, 164 and the o-rings 162, 164 in turn supporting the lower ends of the guide shafts 150, 152. A carriage 170 is carried by the guide shafts 150, 152 and the lead screw 154. The carriage 170 includes holes 172, 174 that receive the guide shafts 150, 152 and which have a diameter such that the carriage slides along and is guided by the guide shafts 150, 152. One of the holes 172, 174 may be fitted with a linear bearing (not shown) and the other such hole may be slightly out-of-round to provide additional clearance as the carriage 170 is moved along the guide shafts 150, 152. The lead screw 154 is threaded into a threaded portion or hole 176 formed in the carriage 170. The threshold 176 may include suitable anti-backlash means (not shown) such as two threaded nuts urged apart by a spring and thus against the threads of the lead screw 154.

Figure 7:
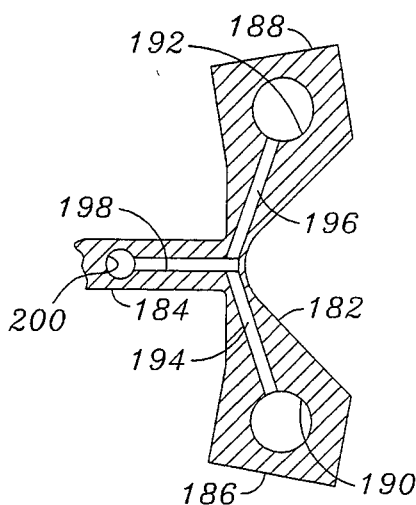
FIG. 7 is a section view of the transport assembly of FIG. 5 taken along 7—7 thereof.
Figure 8:
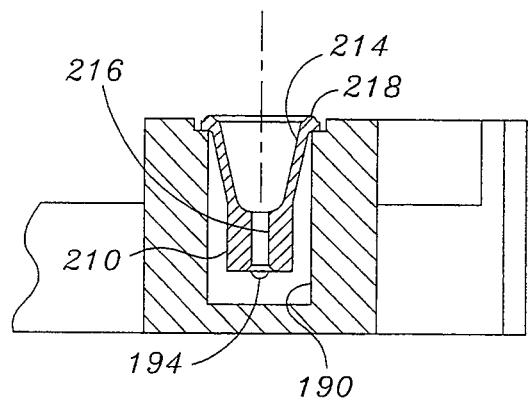
FIG. 8 is a section view of the transport assembly of FIG. 5 taken along 8—8 thereof.

The arm 132 is fixed to the carriage 170 at an attachment portion 180. A receiving means or retaining portion 182 of the arm 132 is formed at the opposite end of the arm from the attachment portion 180, and the arm further includes an extension portion 184 between the attachment portion 180 and the retaining portion 182. The retaining portion 182 includes two opposite projections 186, 188 (FIGS. 5, 7 and 8), the projections including vacuum retaining means for retaining the sample segment 118.

More particularly, the vacuum retaining means includes closed-bottomed bores 190, 192, the bores being open on an upper surface of the projections 186, 188. Conduits 194, 196 lead from the bores to the extension portion 184, and join a conduit 198 formed in the extension portion 184 leading to an opening or port 200 in an upper surface of the extension portion. A length of flexible tubing 202 connects the port 200, and thus the bores 190, 192, to a controlled source of vacuum, which is preferably available from the manifold 106 as is described below. Flexible boots 210, 212 are fixed within the bores 190, 192, the flexible boots 210, 212 including a generally conical or tapered upper portion 214 and a hole 216 through the bottom of the boot (shown in FIG. 8 with respect to the bore 190). Each of the boots 210, 212 also includes a sealing rib 218 formed around the open upper end of the tapered upper portion 214.

Figure 8A:
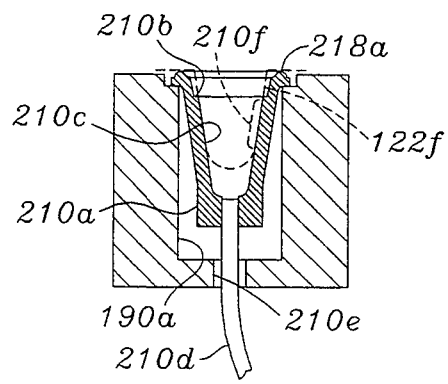
FIG. 8a is another embodiment of the boot and retaining portion of FIG. 8.

An alternative embodiment of the boots 210, 212 is illustrated in FIG. 8a, where one such boot 210a is shown in a bore 190a, similar to the bore 190. The boot 210a is slightly elongated as compared to boot 210 of FIG. 8, and includes an internal shoulder 210b and a reduced conical interior wall 210c as compared to the boot 210. The reduced interior wall 210c is sized to the exterior dimension of, for example, the well 122f shown in phantom in FIG. 8a. As a further alternative, the conduits 194, 196 and 198 are replaced with tubing, such as tubing 210d that passes through a hole 210e in the bore 190a and joins to the tubing 202 (not shown in FIG. 8a). The shoulder 210b and reduced interior wall 210c are adapted to seal against the exterior of the well 122f, providing a large sealing area 210f as compared to a rib 218a, similar to the rib 218 of the embodiment of FIG. 8. In such an embodiment, the rib 218a acts as a secondary or back-up seal. It is also to be appreciated that the rib 218a may be deleted altogether in favor of the shoulder 210b and reduced interior wall 210c.

Continuing with reference to FIGS. 5 and 6, the transport assembly 104 is rotatably mounted to the frame 102, which provides support means for the transport assembly 104, with the bearing 142 retained within an upper cylindrical opening 220 formed into the frame 102. To receive and support the lower end of the transport assembly 104, the frame includes a lower cylindrical opening 222 coaxially aligned with the upper opening 220, the lower opening 222 including a sidewall groove 224. A resilient member such as an o-ring 226, slightly compressed, is disposed between the outer cylindrical surface of the bearing 144 and the groove 224, the o-ring 226 providing a flexible, resilient support between the frame 102 and the bearing 144. The bearings 142, 144 allow rotation of the spindle 130 about the central axis 146. The o-ring 226 provides a resilient mounting that helps to reduce or eliminate the effects of misalignments of the openings 220, 222 that might otherwise cause binding of the carriage 170 through its vertical or translational travel along the guide shafts 150, 152 and lead screw 154, and also helps to reduce noise and vibration that would otherwise be transmitted from the transport assembly 104 to the frame 102.

Motor means in the form of lift and rotation motors 228, 230 respectively are mounted to the frame 102 with suitable brackets (not shown) and drive the transport assembly 104. The motor 228 shaft is connected to the upper end of the lead screw 154 via a flexible coupling 232 (shown via a cut-away in FIG. 5), such as a helical coupling. The lower end of the lead screw 154 is rotatably retained by a bearing 169 that is fixed within the lower support portion 136.

The lead screw 154 and the flexible connector 232 pass through the upper support portion 134, including the gear 140, and thus the lead screw 154 is rotatable independently of the spindle 130. The axis of rotation of the lead screw 154 is coaxial with the spindle central axis 146 and thus provides a translational axis along the axis of rotation of the lead screw 154.

The rotation motor 230 shaft drives a timing belt 234 which in turn drives the gear 140, thereby rotating the spindle 130 and arm 132 about the spindle central axis 146. The motors 228,230 are both conventional stepper motors.

The o-rings 162, 164 provide a resilient, flexible mounting means between the guide shafts 150, 152 and the lower support portion 136. This resilient, flexible support reduces noise and vibration that might otherwise be transferred from the guide shafts 150, 152 to the lower support portion 136. Furthermore, the resilient, flexible characteristic of the o-rings 162, 164 add alignment tolerance between the guide shafts 150, 152 and the lead screw 154 which, along with the flexible coupling 232, minimizes binding as the carriage 170 is moved along the guide shafts 150, 152 and lead screw 154 by rotation of the lead screw 154.

It is seen with reference to FIG. 5 that the attachment portion 180, and in particular the vertical center lines of the boots 210, 212 within the bores 190, 192, are disposed at a predetermined radius 236 with respect to the central axis 146. With rotation and vertical translation of the arm 132 about and along the axis 146, the attachment portion 180 and boots 210, 212 describe a path within the system 100 essentially defined by the radius 236.

With reference now to FIGS. 9–14, the manifold 106 receives and holds the sample segment 118, a plurality of capillary assemblies 240 and fiber optic cables 242, and provides vacuum and fluid manipulation required for electrophoresing samples.

The sample segment 118 is retained at a sample segment receiving station 250. The station includes a segment retaining actuator 252 mounted to the underside of the manifold 106 (as viewed in FIGS. 9 and 10). The actuator includes a solenoid 254 having slotted shaft 256. A pivoted am 257 is pivoted about a pivot point 258 and includes a pressure pad 259 at the outer end of the arm 257. The slotted shaft 256 is coupled to the arm 257 between the pivot point 258 and the pressure pad 259. A spring 259$a$ is wrapped around the pivot point 258 and biases the arm 257 via a claw 259$b$ and thus the pressure pad 259 toward the manifold 106. The pressure pad 259 is adapted to fit the external closed end of the well 122$d$ disposed in the middle of the sample segment 118.

The manifold 106 (FIGS. 9–14) includes suitable means for retaining the capillary assemblies 240 and the optical cables 242. The capillary assemblies 240 include capillaries 260, sample end holders 262 and detection end holders 264. An arcuate sample end retainer 270 is disposed above openings 272 through the manifold 106 and includes sets of clips 274, the sample end retainer 270 being arced to match the radius 236. The clips 274 removably retain the sample end holders 262 with open ends 278 of the capillaries 260 located so as to contact liquid in the wells 122 of the sample segment 118.

Detection end retainers 280 are disposed above openings 282 that are in communication with an electrophoresing conduit 284 formed in the manifold 106. The detection end retainers 280 receive the detection end holders 264 with open ends 286 of the capillaries 260 disposed within the conduit 284. The detection end retainers 280 each include two slides 288 with keyed openings 290. Barrels 292 at the end of the optical cables 242 are inserted through the larger portion of the keyed openings 290, the barrels 292 fitting into recesses 294 in the detection end holders 264 to thus hold the detection end holders 264 within the recesses 294. The recesses including openings (not shown) that expose the capillary 260. The slides 288 are moved to slide the smaller portion of the keyed opening 290 into a groove 294 in the barrel 292, thus retaining the barrel 292 within the detection end retainer 280. The barrels 292 direct optical energy from optical fibers in the optical cables 242 through the capillary 260 and receive such energy from the capillary 260, all as is well known in the art. Other suitable capillary assembly and optical cable retaining means may also be used.

Figure 9:
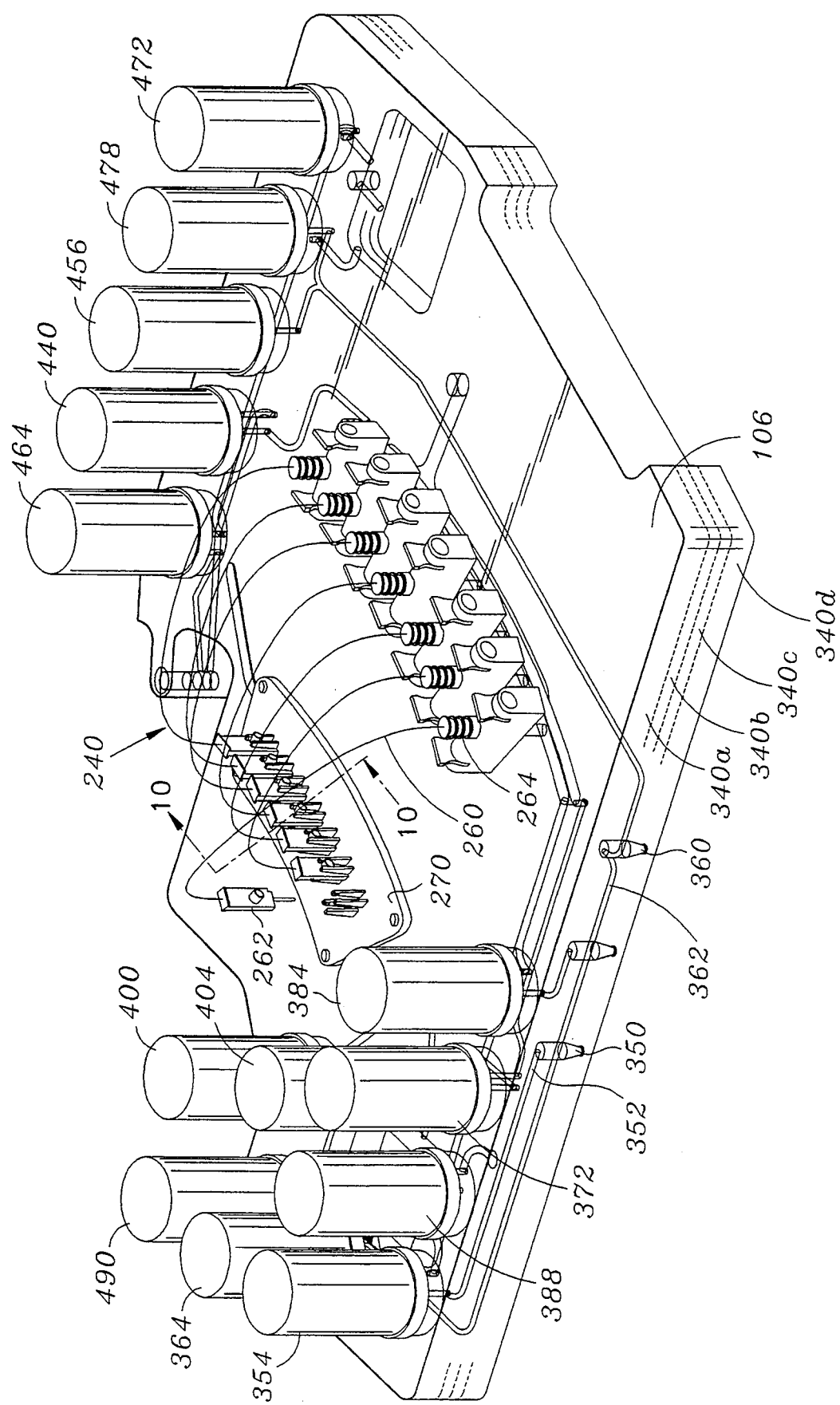
FIG. 9 is a perspective view of the manifold of the system of FIG. 1.
Figure 11:
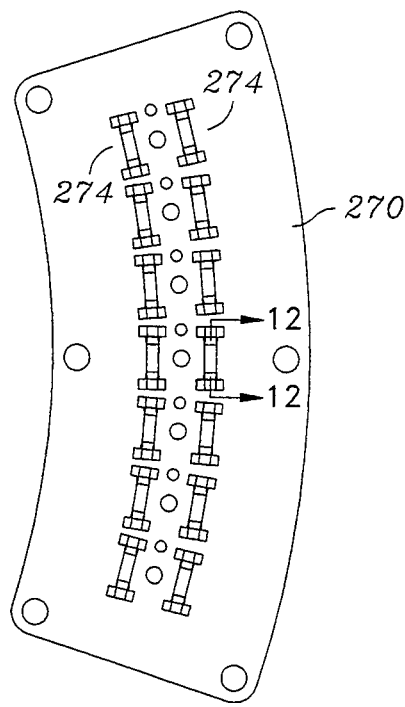
FIG. 11 is a top view of a sample end retainer used on the manifold of FIG. 9.
Figure 12:
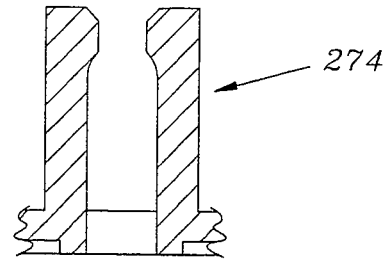
FIG. 12 is a section view of the sample end retainer of FIG. 11 taken along line 12—12 thereof.
Figure 13:
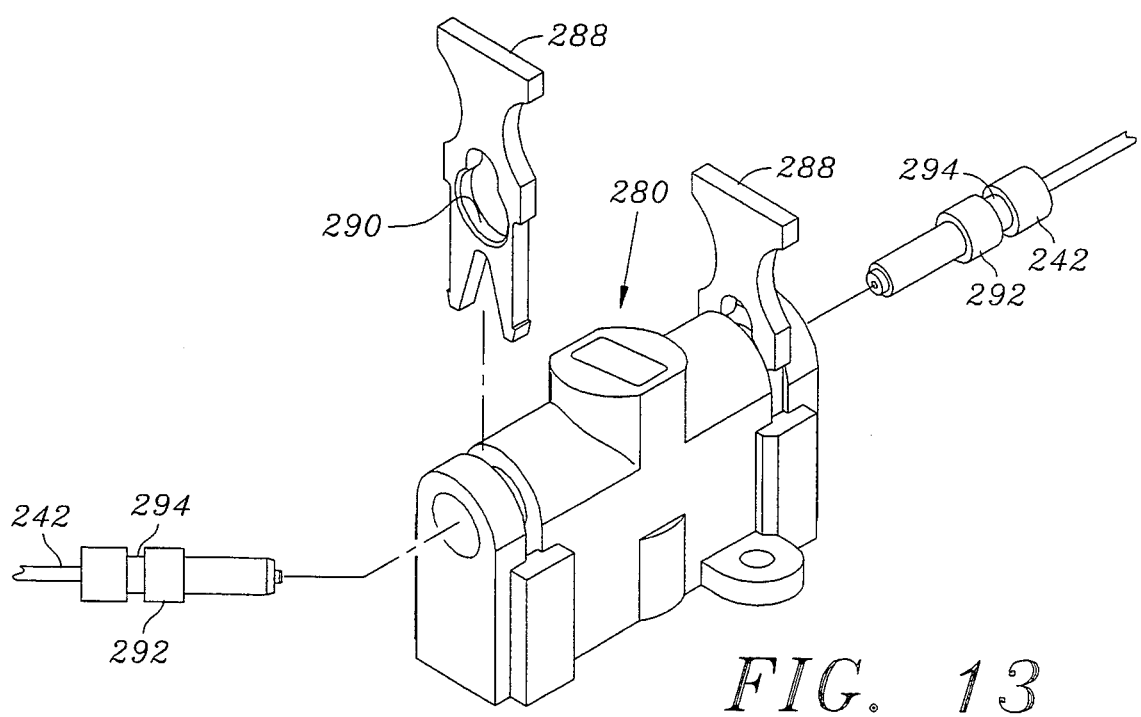
FIG. 13 is a perspective view of a detection end retainer used on the manifold of FIG. 9.
Figure 14:
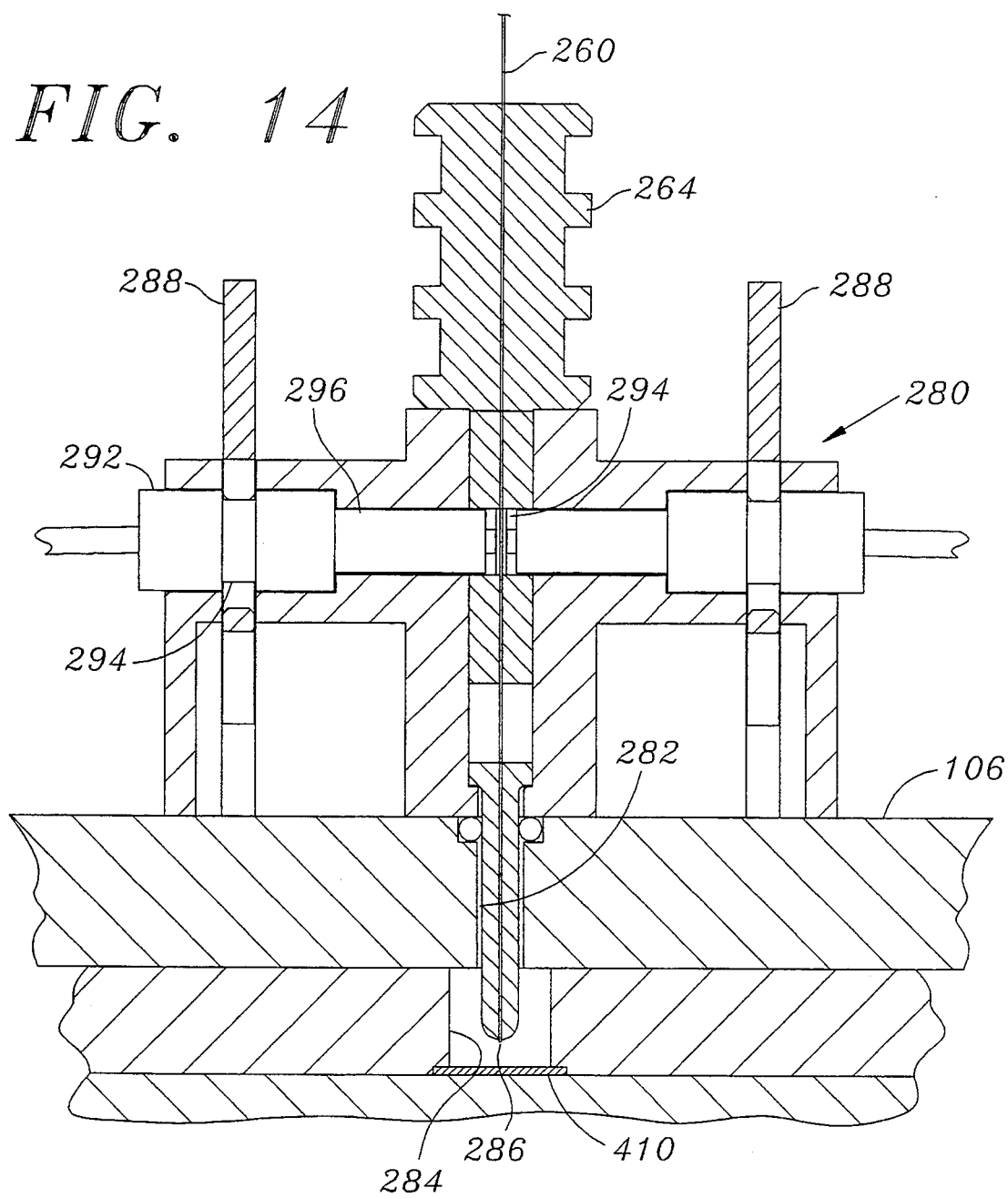
FIG. 14 is a partial section view of the detection end retainer of FIG. 13 with a capillary assembly and optical cables installed.

The manifold 106 includes means for providing buffer to the conduit 284, including various ports, conduits, valves and a reservoir. Preferably the manifold 106 is formed from four acrylic layers 340$a$–340$d$ (FIGS. 9 and 15) into which various conduits, ports, reservoirs and the like and formed, the layer 340$a$ being the top or uppermost as seen in FIG. 9. The layers 340$a$–340$d$ are then aligned and bonded together with the application of heat and force.

Figure 16:
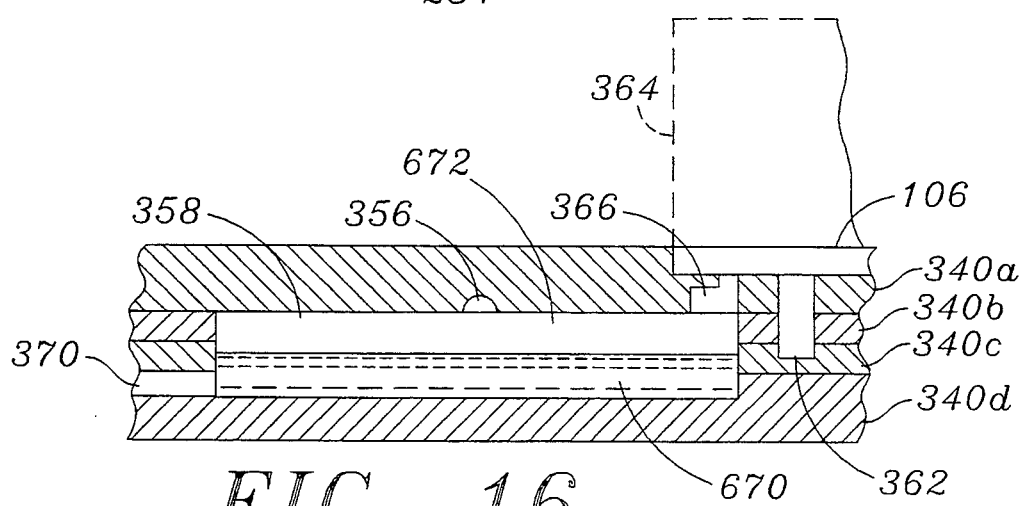
FIG. 16 is a section view of the manifold of FIG. 15 taken along line 16—16 thereof.
Figure 15:
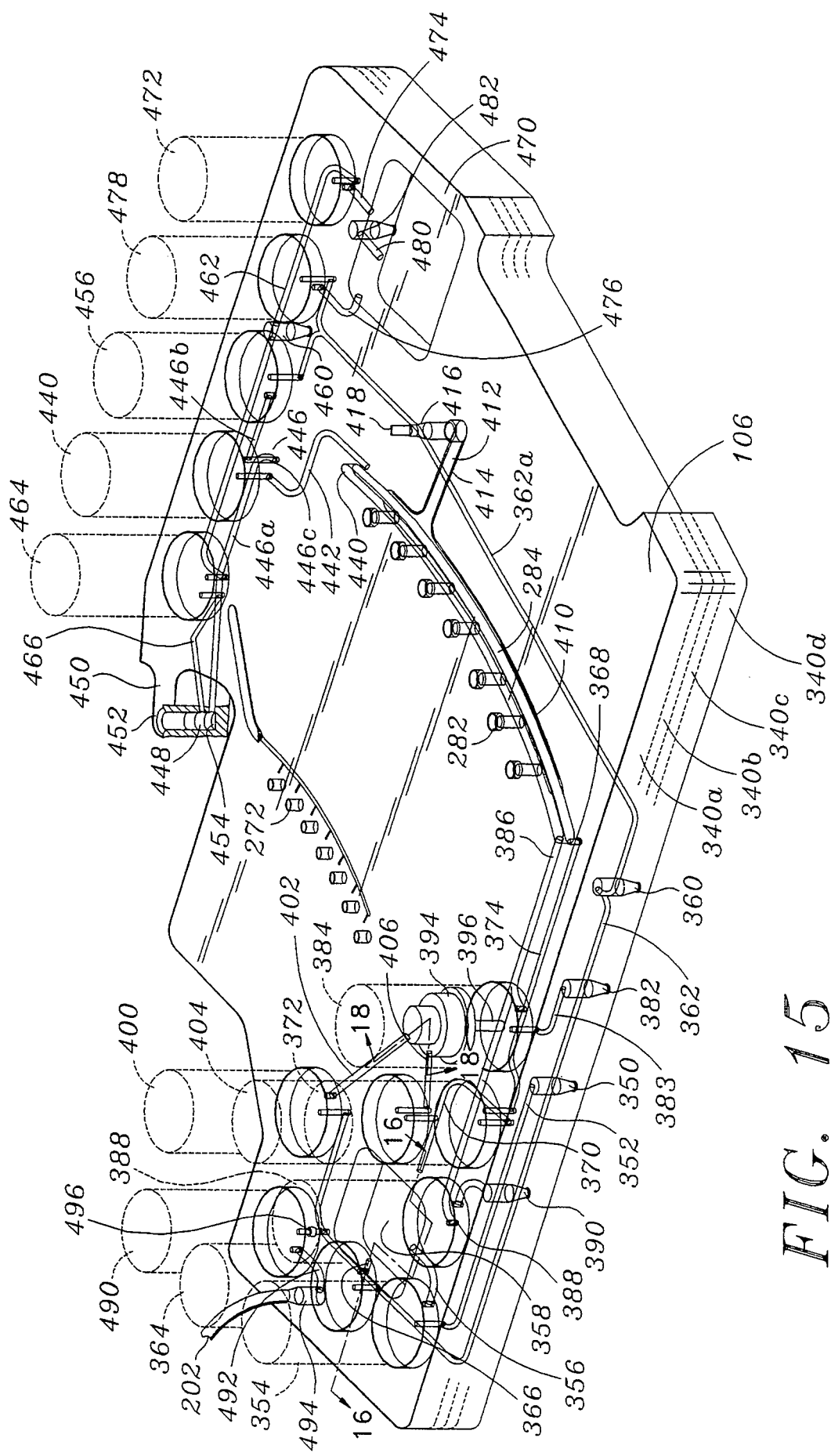
FIG. 15 is a simplified view of the manifold of FIG. 9 with the sample end retainer and detection end retainers removed and the valves in phantom, illustrating various fluid conduits.

With reference to FIG. 15, a liquid buffer port 350 is connected via a conduit 352 to a buffer input valve 354. The output of the buffer input valve 354 is connected via a conduit 356 to a closed buffer de-gas reservoir 358 formed internally within the manifold 106. The de-gas reservoir 358 as seen in FIG. 16 is enclosed within the manifold 106. The dimensions of the de-gas reservoir 358 are such that the reservoir 358 is relatively shallow. In the particular embodiment disclosed herein, the de-gas reservoir 358 is about 1.5 inch wide, about 1.25 inch long, and about 0.40 inch high, all formed within and enclosed by the manifold 106. As seen in FIG. 16, the conduit 356 enters the a first end or top of the reservoir 358, the conduit 356 being formed into the lower surface of the first layer 340a. Vacuum is also applied to the reservoir 358 via an unregulated vacuum port 360, conduit 362, buffer vacuum valve 364 and conduit 366. The conduit 366, as with the conduit 356, enters the top of the reservoir 358.

Figure 17:
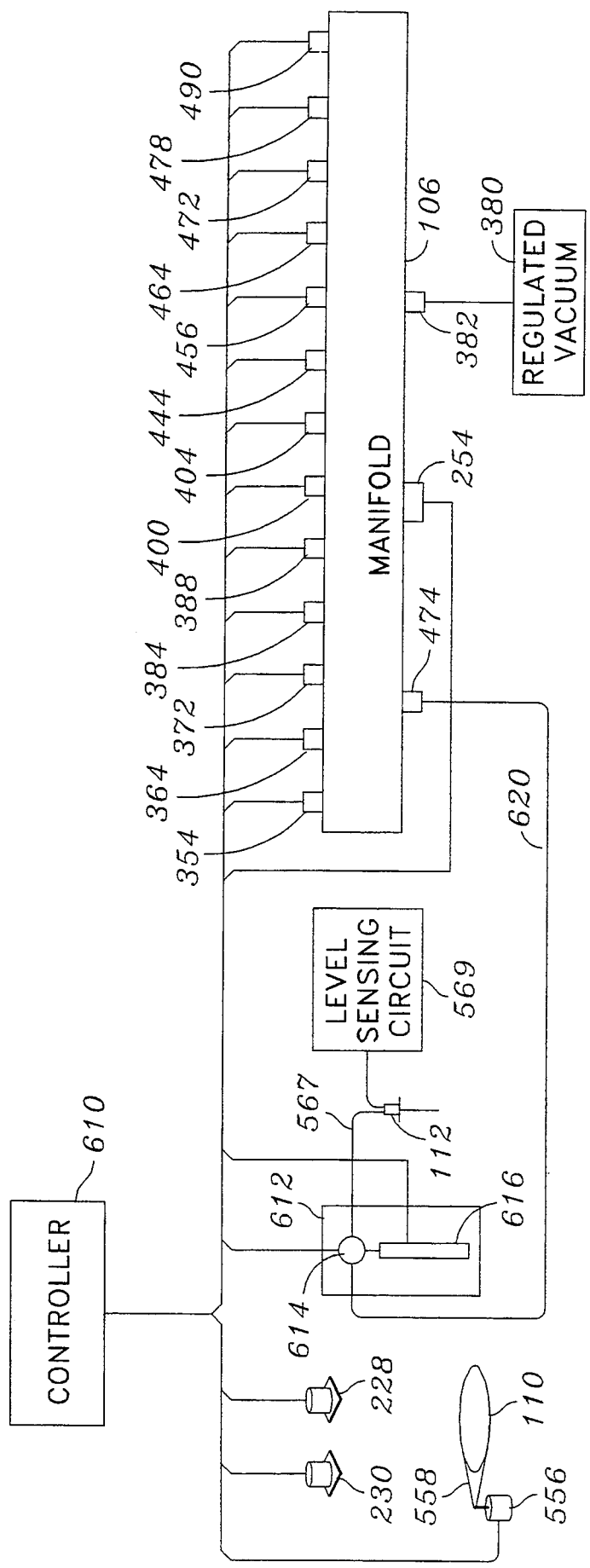
FIG. 17 is a simplified functional diagram of an analyzer in which the system of the present invention may be used.

Buffer from the de-gas reservoir 358 is supplied to buffer supply end 368 of the electrophoresing conduit 284 by means of a conduit 370, de-gassed buffer valve 372 and a conduit 374. The conduit 370 is formed in the fourth layer 340d and thus opens into the reservoir 358 at a second end or at the bottom of the reservoir 358 (FIG. 16). The buffer supply end 368 is also controllably connected to vacuum means in part formed by a source of regulated vacuum 380 (shown diagrammatically in FIG. 17) via regulated vacuum port 382, conduit 383, inlet vacuum valve 384 and conduit 386. The conduit 386 is also in communication with a vent valve 388 which in turn is in communication with a vent port 390. The vent port 390 may be connected to a vent tube (not shown) which has an open end located to provide a vent to atmosphere without overflow of any gravity or pressure fed liquids supplied to the manifold 106, such as buffer or deionized water.

Figure 18:
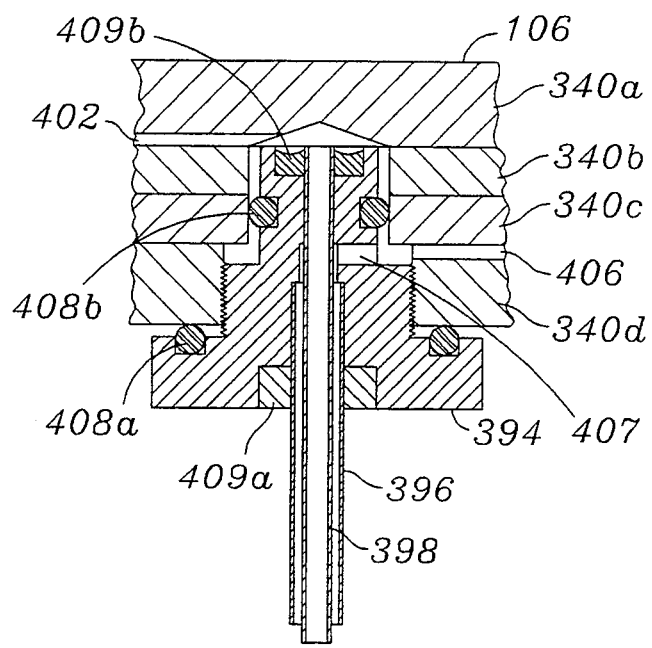
FIG. 18 is a section view of the manifold of FIG. 15 taken along line 18—18 thereof.

The manifold 106 includes a coaxial probe assembly 394 (FIG. 18) including a running buffer dispensing probe 396 and a vacuum probe 398, the dispensing probe 396 being concentrically disposed and external with respect to a vacuum probe 398. Unregulated vacuum is supplied via the conduit 362, a probe vacuum valve 400, and a conduit 402. De-gassed running buffer from the reservoir 358 is supplied via the conduit 370 to a probe buffer valve 404 and then via a conduit 406 and a probe internal conduit 407 to the probe 396. O-ring 408a seals the coaxial probe assembly 394 within the manifold 106, and o-ring 408b provides a seal between the upper vacuum and lower buffer portions of the coaxial probe assembly 394. Adhesive 409a, 409b fixes the dispensing probe 396 and the vacuum probe 398, respectively, within the coaxial probe assembly 394.

A conduit electrode 410 (FIGS. 14 and 15) is disposed within the electrophoresing conduit 284. The conduit electrode 410 has an arm 412 extending laterally from a main portion of the conduit electrode 410 within the conduit 284. The arm 412 is contained within a cavity 414 formed in the manifold 106 and is in contact with a spring loaded electrical contact 416 that is threaded into the manifold 106, the contact 416 forming a fluid-tight seal with the manifold 106 and providing a connecting terminal 418 to which one potential of the electrophoresing voltage may be connected. The conduit electrode 410 is preferably formed from sheet stainless steel shim stock approximately 0.004 inch thick, and is thus exceptionally robust and long-lasting.

Figure 10:
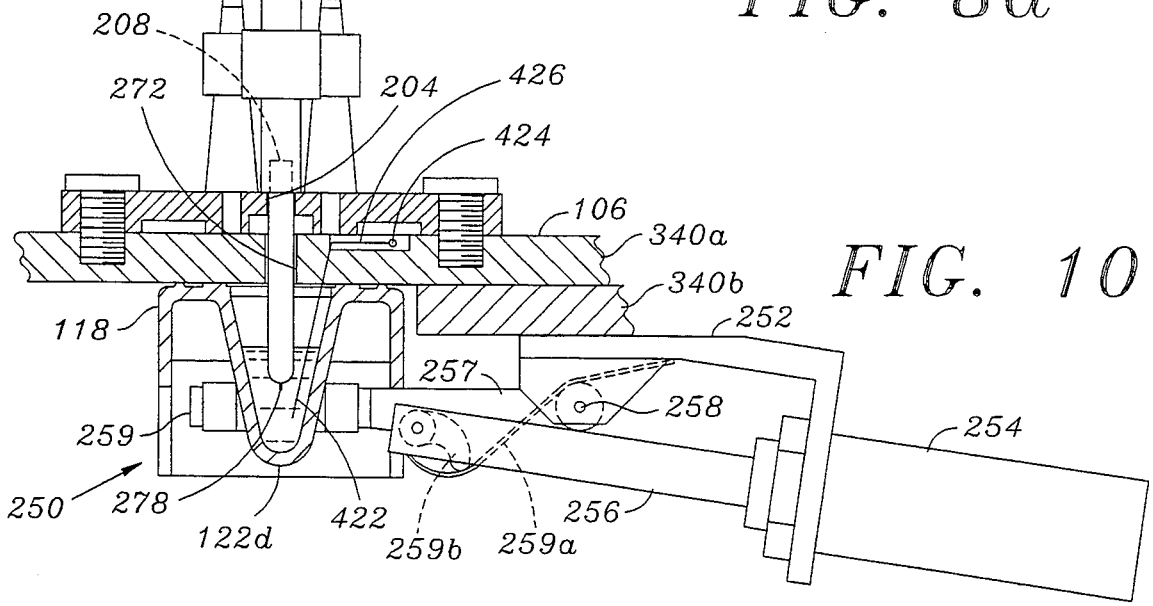
FIG. 10 is a section view of the manifold of FIG. 9 taken along line 10—10 thereof.

High voltage for electrophoresing is applied to liquids contained in the wells 122 of the sample segment 118 retained at the receiving station 250 by means of individual palladium well electrodes 422 (FIG. 10). The electrodes 422 are connected to a high voltage supply wire 424 cemented into a groove 426 formed into the upper surface of the first layer 340a, the wire 424 being connected to a suitable controlled high voltage supply (not shown).

A second end 440 of the electrophoresing conduit 284 is connected via a conduit 442 to the input of a conduit valve 444. The conduit valve 444 output is connected to a conduit 446, a portion 446a of the conduit 446 being formed in the fourth layer 340c, a second portion 446b of the conduit 446 being formed in the first layer 340a, the portions 446a and 446b being connected by a vertical portion 446c formed through the second and third layers 340b, 340c. The portion 446a of the conduit 446 in turn feeds into a lower portion of a wash cell 448 shown partially in cut-away in FIG. 15, the wash cell 448 being formed in an protruding portion of the manifold 106. The wash cell 448 includes a tapered opening 452 and a closed bottom 454. An extension 362a of the vacuum conduit 362 may be in communication with the portion 446b of the conduit 446 via a wash vacuum valve 456.

Deionized water is supplied to the manifold 106 via a port 460 which is in communication with a conduit 462. The conduit 462 is connected to one port of a wash valve 464, the other port of the valve 464 being in communication with the wash cell 448 via a conduit 466. The conduit 446 is formed in the third layer 340c, and thus enters the wash cell 448 above the conduit 446a. The conduit 446 may also be formed in the second or third layer 340b, 340c, thus providing an increased wash fluid height within the wash cell 448.

Deionized water is also supplied to a second de-gassing reservoir 470 formed internally within the manifold 106 via the conduit 462 which is controllably connected through an inlet valve 472 and a conduit 474. In the particular embodiment disclosed herein, the second de-gassing reservoir 470 is about 1.75 inch wide by about 1.75 inch long by about 0.40 inch high. The conduit 474 is formed in the first layer 340a, and thus enters the top of the reservoir 470. De-gassing vacuum is applied to the reservoir 470 via a conduit 476 controllably connected through a water de-gas valve 478 to the conduit extension 362a. De-gassed water from the reservoir 470 is removed via a conduit 480 that is formed in the fourth layer 340d and thus enters the lower portion of the reservoir 470, the conduit leading to a de-gassed water port 482 for use elsewhere such as, for example, in the pipette probe 112.

The manifold 106 also supplies controlled vacuum to the bores 190, 192. A pickup valve 490 includes a port in communication with the unregulated vacuum conduit 362, the other port of the valve 490 being is communication with a conduit 492 leading to a port 494 which is in turn connected to the tubing 202 leading to the bores 190, 192 as described above. The valve 490 is a three-way poppit type valve which either applies vacuum from the conduit 362 to the tubing 202, or vents the tubing 202, and thus the bores 190, 192 to atmosphere. A check valve 496 may be included in the vacuum supply to the pick-up valve 490 to prevent vacuum applied to the arm 132 from being varied, and thus the gripping force of the retaining portion 182 reduced, by variations in the vacuum available in the conduit 362.

Figure 19:
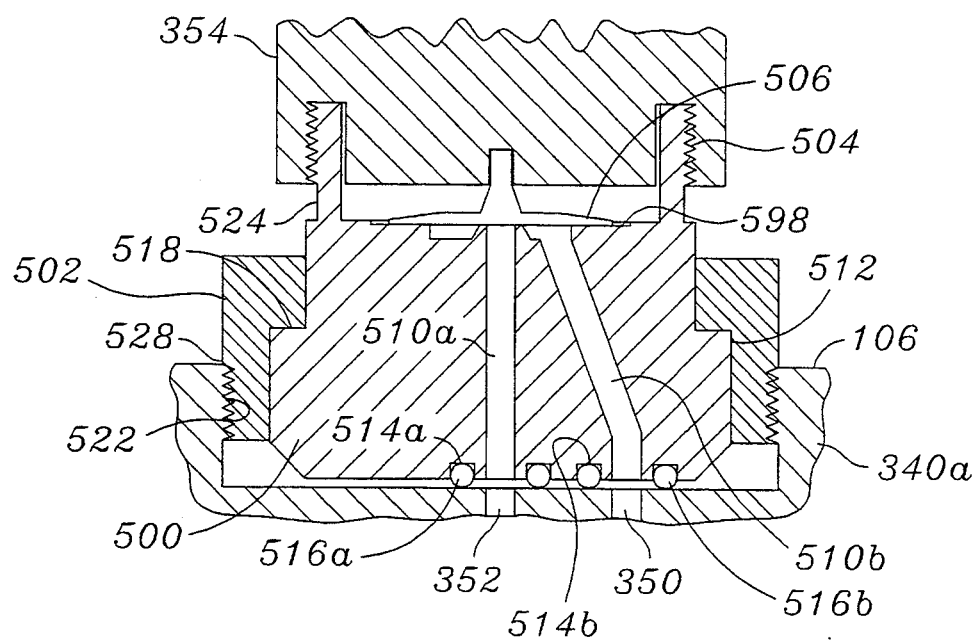
FIG. 19 is a section view of a valve adapter used with the manifold of FIG. 15 taken along line 19—19 of FIG. 15.

The valves mounted to the manifold 106 are each mounted via a valve adapter 500 and retainer ring 502 (FIG. 19) illustrated with respect to buffer input valve 354. The adapter includes a threaded upper neck 504 that receives the buffer input valve 354. The buffer input valve 354 includes a rubber diaphragm 506 that is normally seated against a valve seat 508 internal of the neck 504. Two conduits 510a, 510b provide fluid communication between the valve seat 508 and a base 512 of the adapter 500. Annular grooves 514a, 514b surround the open ends of the conduits 510a, 510b, and receive o-rings 516a, 516b which form a seal between the base 512 and the manifold 106, connecting, for example, the manifold conduit 352 to the conduit 510a, and the manifold conduit 350 to the conduit 510b.

The retainer ring 502 engages an annular surface 518 of the adapter 500 and has external threads 520 that engage internal threads 522 on the manifold. The threaded neck 504 which is threaded to the buffer input valve 354 has a reduced portion 524 between the threaded portion of the neck 504 and the body of the adapter 500. This reduced portion is adapted to fail if the buffer input valve 354 is struck as, for example, during maintenance of the analyzer in which the manifold 106 is disposed. Such a failure causes the buffer input valve 354 to break free of the adapter 500. The adapter 500 can then be simply replaced, saving the manifold internal threads 522 from damage. Thus, only the adapter 500 need be replaced, rather than the much more expensive manifold 106.

For the sake of clarity, it is to be noted that the ports 390, 350, 382, 360 and 460 are threaded into the bottom surface of the manifold 106 (as viewed in FIG. 15).

As described above, the sample wheel 110 is adapted to support the sectors 114 and sample segments 118. Sector mounting supports 540 (FIG. 1) are formed about the periphery of the sample wheel 110, each of the supports 110 including support members 542a, 542b which in turn define tapered pins 544a, 544b that are shaped to fit corresponding tapered holes (not shown) in a sector 114 to thereby hang and removably retain the sector 114 from the sample wheel 110.

Sample segment supports 546 are defined between each of the sector mounting supports 540. Arcuate openings 548 are formed through the sample wheel 110 internal of the sector mounting supports 540, the size and shape of the openings 548 being adapted to receive and index the sample segments 118 in the sample wheel 110. Ledges 550 at both ends of the openings 548 support the ends of the sample segment arcuate body 120.

A radial access slot 552 provides access to the arcuate openings 548 from the outer edge of the sample wheel 110, the slot 552 being aligned with and generally perpendicular to the center of the arcuate opening 548. The slot 552 is sized to receive the extension portion 184 of the sample handling arm 132, the arcuate opening 548 being likewise sized to receive the retaining portion 182 of the arm 132, thus enabling removal or replacement of a sample segment 118 from or onto the sample wheel 110 by the sample handling arm 132 as is described hereinbelow. It is to be appreciated that the slot 552 in the sample wheel 110 need not be radial. In such an instance, the am 132 could be curved to accommodate a non-radial slot 552.

The sample wheel 110 is supported about a central rotational axis 554 and is rotated by means of a sample wheel motor 556 and belt 558 (illustrated in diagram form in FIG. 17) in a conventional fashion. The sample wheel 110 is supported vertically with respect to the transport assembly 104 such that the arm 132 may be freely rotated about the central axis 146 above and below the sample wheel 110. The sample wheel 110 may be formed, for example, by structural foam molding.

Figure 20:
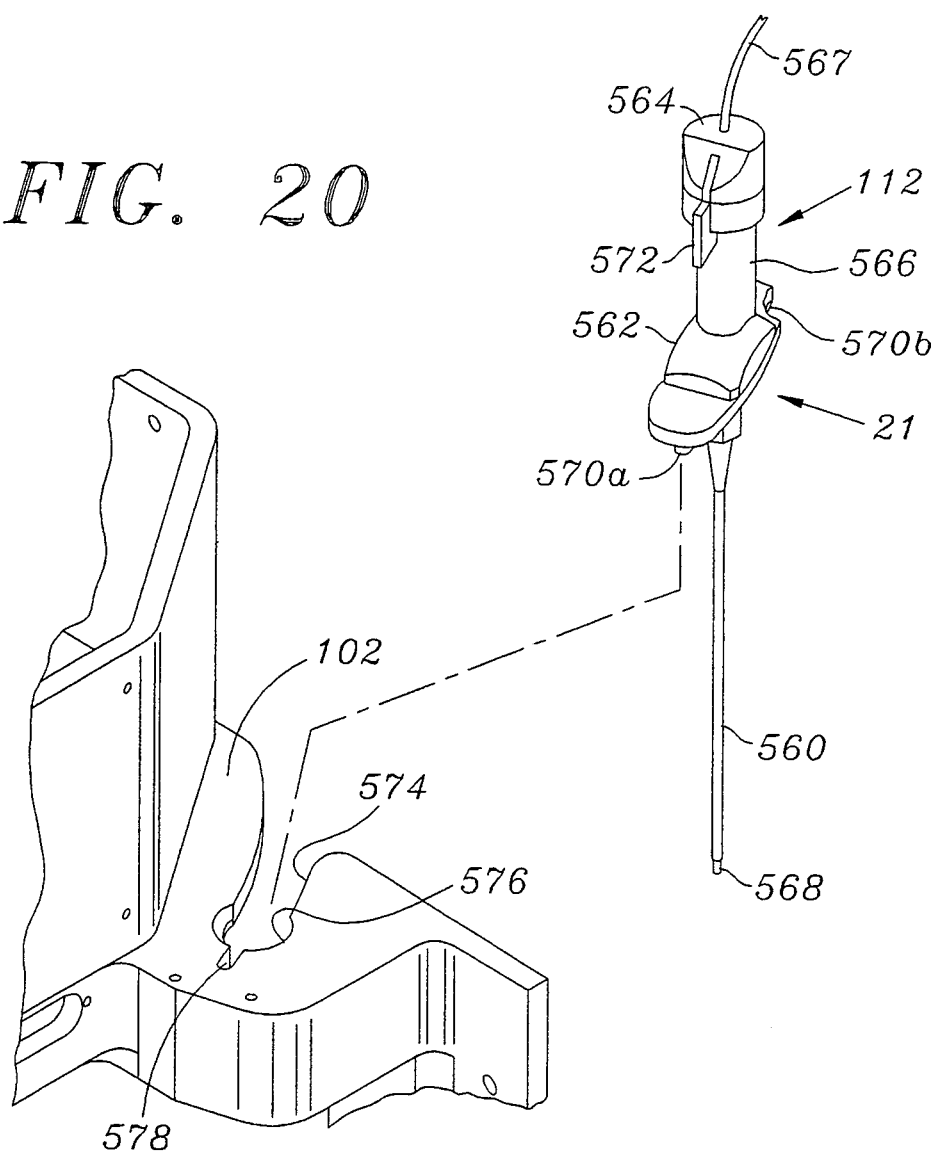
FIG. 20 is a perspective view of a pipette probe which may be part of the system of the present invention.
Figure 23:
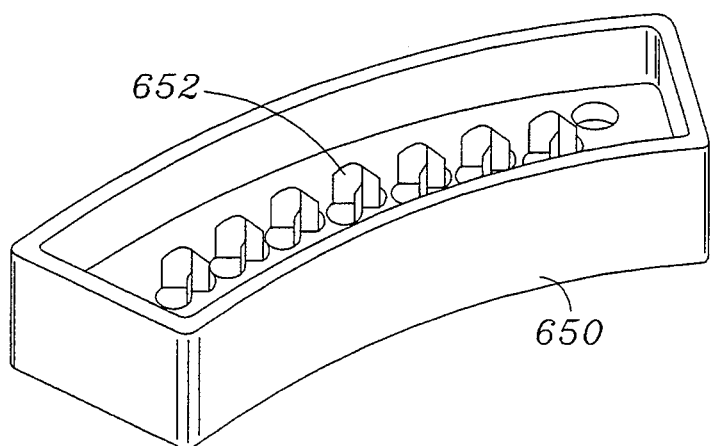
FIG. 23 is a perspective view of a knife assembly, rotated for a view of the knives thereof.
Figure 21:
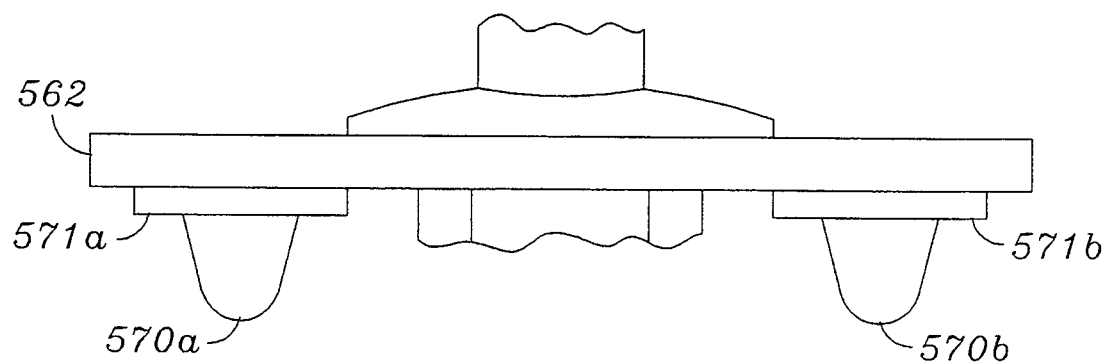
FIG. 21 is a side view of the pipette probe flange of FIG. 20 taken from the direction of arrow 21 thereof.
Figure 22:
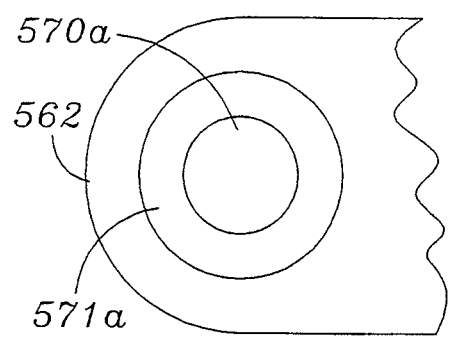
FIG. 22 is a bottom view of one of the projections and flat annular surfaces of the flange FIG. 21.

The pipette probe 112 (FIG. 17, 20) hangs from the frame 102 when not in use. The pipette probe 112 generally includes a hollow tube 560, a flange 562 above the tube 560 (when oriented as illustrated in FIG. 20), a keyed head 564 at the top of the pipette probe 112, and a reduced barrel portion 566 between the flange 562 and the head 564. The tube 560 is preferably stainless steel and is lined with tubing 567 and has an open tip 568 extending about 0.050 inch out of the tube 560 and through which liquids may be aspirated and discharged. The flange 562 extends laterally and includes two tapered downwardly extending projections 570a, 570b, (FIGS. 20–22) which are essentially the same exterior size and shape as are the wells 112b, 112f of the sample segment 118. Two flat annular surfaces 571a, 571b around the projections 570a, 570b are likewise essentially identical to the flat annular surfaces 124, 125 formed around the wells 122b, 122f. Thus, the projections 570a, 570b and the annular surfaces 571a, 571b are adapted to be removably received and retained by the arm 132 within the bores 190, 192 and the boots 210, 212.

The head 564 includes a key 572 projecting to the side of the head 564. The barrel portion 566 is sized to fit through a slot 574 and opening 576 formed in the frame 102, the opening 576 including a keyway 578 that receives the key 572. The opening 576 is smaller in diameter than the head 564 such that the pipette probe 112 may be supported by the head 564 within the opening 576, the key 572 and keyway 578 cooperating to align the pipette probe 112 within the opening 576 and thus with respect to the frame 102. With the pipette probe 112 so disposed, the probe tip 568 is disposed within the wash cell 448, with the tip 568 about 0.050 inch from the closed bottom 454.

The pipette probe 112 is connected to level sensing means, such as a level sensing circuit 569 (FIG. 17) to sense the contact of the tube 560 with liquid. The level sensing circuit 569 means may be of any suitable design. In the embodiment disclosed herein, the level sensing circuit 569 may include rf level sensing such as disclosed in U.S. Pat. No. 4,912,976, which is incorporated herein by reference, with ferrite reactive elements disclosed in such patent contained within the barrel portion 566.

A control means or controller 610 (FIG. 17) is used to control the operation of the sample handling system 100. The controller 610 may include, for example, a microprocessor as is well known in the art to control the lift and rotation motors 228, 230, sample wheel motor 556, manifold valves 354, 364, 372, 384, 388, 400, 404, 444, 456, 464, 472, 478 and 490, and receiving station solenoid 254. The controller also controls a pipettor-dilutor 612, shown diagrammatically in FIG. 17, including a motor-controlled valve 614 and a motor-controlled precision syringe 616. The valve is connected by the tubing 567 to the pipette probe 112 and by tubing 620 to the de-gassed water port 474 on the manifold 106. The controller 610 and pipettor-dilutor 612 may be of conventional design of the type well known in the art.

A label piercing knife assembly 650 (FIGS. 1, 21) may be used to pierce the labels 129. The knife assembly 650 is mounted to the frame 102, the knife assembly 650 including sets of cross-cut knives 652, the sets of knives 652 being directed downwardly and spaced as are the wells 122a–122g. Furthermore, a removable reagent holder 662 is removably received by the frame 102. The holder 662 is adapted to hold two open reagent containers 664, 668 from which reagents may be dispensed by means of the pipette probe 112.

The arcuate opening 548 (when the associated slot 552 is aligned to receive the arm 132), the probes 396, 398 of the coaxial probe assembly 394, the sample receiving station 250 and the holding stations 630, 640 are all disposed along the radius 236. Thus, these elements are all adapted to be accessed by a sample segment 118 carried by the arm 132 at the attachment portion 180. The pipette probe 112 when retained at the opening 576, and specifically the projections 570a, 570b, is also disposed at the radius 236, accordingly enabling the pipette probe 112 to be picked up and transported by the attachment portion 180 such that the tip 568 is then also disposed at the radius 236. Further, the open tops of the reagent containers 662, 664 and the open wells 122 of sample segments 118 disposed at the holding stations 630, 640 are also disposed along the radius 236. This allows the pipette probe 112 to be used to transfer liquids to and from such containers.

In operation, the transport assembly 104 operates to move sample segments 118 between the sample wheel 110 and the manifold 106, and also may deposit sample segments at intermediate holding stations 630, 640. Each of the holding stations 630, 640 is configured similarly to the sample segment supports 546 and slots 552 described above with respect to the sample wheel 110.

For example, to move a sample segment 118 from the sample wheel 110 to the manifold 106, the sample wheel 110 is first rotated to position one of the sample segments 118 to a pick-up position 669. At the pick-up position 669, the associated slot 552 is aligned with the transport assembly 104, that is, the slot 552 is on a line between the axis 146 of the spindle 130 and the rotational axis 554 of the sample wheel. With the sample handling arm 132 initially in a position below the sample wheel 110, the rotation motor 230 is controlled so as to rotate the gear 140 and thus the spindle 130 to align the sample handling arm 132 with the slot. The lift motor 228 is controlled to rotate the lead screw 154 to raise the carriage 170 and thus the arm 132 through the slot 552, such that the wells 122b, 122f that include the annular surfaces 124, 125 are received within the boots 210, 212. Pickup valve 490 is energized, applying vacuum to the interior of the boots 210, 212 and thus holding the wells 122b, 122f within the boots 210, 212. The flexible nature of the boots 210, 212 and the seal formed between the annular surfaces 124, 125 and the sealing rib 218 defined by the boots positively retains the sample segment 118 on the retaining portion 182 of the sample handling arm 132.

The lift motor 228 is operated to lift the arm 132 and segment 118 above the upper surface of the sample wheel 110. The rotation motor 230 may be controlled by the controller 610 to rapidly vibrate or agitate the arm 132. This agitation is particularly useful for mixing the samples for reaction with the reagents 126 or, if the reagents 126 are to be reconstituted by the addition of water or buffer, for the reconstitution of the reagents 126. The agitation produces a rapid vortexing flow within the wells 122. With the mixing element 128 in a well 122, this rapid vortexing and the swirling and mixing action of the mixing element 128 produces a complete and effective mixing action.

With the agitation completed, or if no agitation is required, the rotation motor 230 is operated to rotate the spindle 130 so as to align the arm 132 and segment 118 immediately below the receiving station 250. The solenoid 254 is energized, retracting the arm 257 and pressure pad 259. The lift motor 228 is again operated, raising the segment 118 up against the bottom of the manifold 106 and the solenoid 254 is released, the pressure pad 259 clamping the segment 118 at the receiving station 250. With the capillary assemblies 240 installed on the manifold 106, the open ends 278 extend into the wells 122 along with the electrodes 422. Liquid in the wells 122, such as buffer or a diluted sample, can then be drawn into the capillaries 260 by the application, for example, of regulated vacuum to the electrophoresing conduit 284 via operation of the inlet vacuum valve 384. Alternatively, electrophoresing voltage can be applied across the capillary assemblies 240 via the well electrodes 422 and the conduit electrode 410.

Similarly, spindle 130 rotation and arm 132 vertical displacement can move sample segments 118 from the manifold 106 to the sample wheel 110 or to one of the holding stations 630, 640. Furthermore, such operation can move a sample segment 118 that has a label 129 to the label piercing knife assembly 650 mounted to the frame 102. By raising a label-covered segment 118 up against the knife assembly, X-shaped cuts are made into the label 129 by means of the cross-cut knives 652, opening the wells 122 for further liquid transfers and for positioning of the segment 118 at the receiving station 250 as described above.

Sample segments 118 may also be transported such that a selected well 122 is positioned below the coaxial probe assembly 394. Operation of the probe buffer valve 404 supplies buffer to the selected well 122. By performing this operation, the wells 122 of a clean sample segment 118 are filled with running buffer. The sample segment 118 can then be disposed at the receiving station 250 (by operation of the transport assembly 104 as described above) and, by application of vacuum to the conduit 284, running buffer is drawn into the capillaries 260.

Likewise, operation of the probe vacuum valve 400 is used to vacuum aspirate the contents of a selected well 122 as, for example, may be required to clean out the wells 122 of a segment 118 before returning the segment 118 to the sample wheel 110.

The transfer assembly 104 is also operated to transport the pipette probe 112 for various pipetting operations. Particularly, the lift and rotation motors 228 and 230 are controlled to rotate the spindle 130 to a position with the bores 190, 192 and the boots 210, 212 vertically aligned beneath the projections 570a, 570b. The lift motor 228 is controlled to raise the carriage 170 and arm 132 such that the boots 210, 212 contact the hold the projections 570a, 570b, respectively. Pickup valve 490 is energized, applying vacuum to the interior of the boots 210, 212 and thus holding the projections 570a, 570b and the pipette probe 112 firmly to the retaining portion 182 of the sample handling arm 132.

The lift motor 228 is further controlled to raise the pipette probe 112 sufficiently such that the head 564 is clear of the opening 576. The lift motor 228 is stopped and the rotation motor 230 is controlled to rotate the spindle 130 and thus the arm 132 as required. For example, the rotation motor 230 and the wheel motor 556 are operated to position a sample-containing test tube 116 beneath the pipette probe 112. The pipette probe 112 is lowered by operation of the lift motor 228 into the test tube 116, the level detection circuit 569 indicating contact with sample in the test tube 116. The pipettor-dilutor 612 is operated to aspirate sample into the tube 560, and the lift motor 228 is operated to withdraw the tube 560 from the test tube 116.

The rotation and wheel motors 230 and 556 are again controlled to position the pipette probe 112 above a selected well 122 in a selected sample segment 118 on the sample wheel 110. The lift motor 228 is operated to lower the tip 568 into the selected well 122 and the sample is dispensed into the selected well 122 by operation of the pipettor-dilutor 612.

Similar operations are executed to, for example, further serially dilute a sample in a selected well 122 to additional wells 122 in the selected sample segment 118 by operation of the motors 228, 230 and 556, along with the pipettor-dilutor 612. Such an operation may be required, for example, in immunosubtraction electrophoresis, such as is disclosed in U.S. patent application Ser. No. 07/916,313, now U.S. Pat. No. 5,228,960 filed Jul. 17, 1992, and entitled "Analysis of Samples by Capillary Electrophoretic Immunosubtraction," and which is incorporated herein by reference.

Reagents from the reagent containers 664, 668 may also be dispensed by the pipette probe 112 into sample segments 118 held at the holding station 630 or, alternatively, sample segments 118 on the sample wheel 110. Such reagents may include, for example, sodium hydroxide used to clean the capillaries 260 after an idle period or after an analysis of samples. As a further alternative, reagents and/or samples contained in the sample segments 118 held at the holding stations 630, 640 may be transferred to the sample segments 118 on the sample wheel 110.

It is to be appreciated that a sample segment 118 positioned for pickup by the arm 132, the pipette probe 112 when received within the opening 576, the knife assembly 650, the reagent bottles 664, 668 the holding stations 630, 640, the coaxial probe assembly 394, and the receiving station 250 lie along a travel path of the retaining portion 182 and particularly of the boots 210, 212. This travel path may be considered as describing a portion of a cylinder centered along the central axis 146 with a radius equal to the radius 236. With such an advantageous arrangement, the arm 132 provides an effective combination of functions, such as sample segment 118 transportation, pipetting, buffer dispensing and vacuum aspiration, and label piercing with a single transportation assembly 104, simplifying the system 100 while retaining significant analytical throughput.

Running buffer 670 supplied to the de-gassing reservoir 358 as described above partially fills the reservoir 358 because air 672 is trapped at the upper portion of the reservoir 358. Vacuum applied to the reservoir by operation of the buffer vacuum valve 364 causes dissolved gas in the buffer 670 within the reservoir 358 is rapidly bubble out of solution, thus rapidly degassing the volume of buffer 670 within the buffer degas reservoir 358. Buffer vacuum valve 364 is operated only when the remaining valves in communication with the reservoir 358, namely valves 354, 404, and 372, are closed.

It is believed the rapid de-gassing of the buffer 670 occurs because the surface area of the buffer 670 within the reservoir 358 is large with respect to the volume of buffer contained within the reservoir, that is, the buffer is relatively shallow. For example with respect to the particular embodiment disclosed herein and without being bound to the particular dimensions and ratios disclosed herein, the surface area of the buffer contained within the reservoir 358 is about 1.875 square inch, and the volume of such buffer when the reservoir 358 is about half full, is about 0.375 cubic inch, or a ratio of surface area to retained liquid volume of about five. The overall volume of the reservoir 358 is about 0.75 cubic inch, and thus the ratio of surface area to overall volume is about two and one half. Other dimensions that provide a relatively shallow body of buffer may also be suitable. Accordingly, buffer drawn from the bottom of the reservoir 358 via the conduit 370 is thus substantially gas free and is supplied, for example, by the degassed buffer valve 372 to fill the electrophoresing conduit 284 and via the probe buffer valve 404 through the dispensing probe 396.

The water de-gassing reservoir 470 operates similarly, providing de-gassed de-ionized water to the pipettor-dilutor 612. Again with respect to the particular embodiment disclosed herein and without being bound by the particular dimensions and ratios disclosed herein, the surface area of de-ionized water within the reservoir 470 is about 3.06 square inches and the volume of such water when the reservoir 470 is about half full is about 0.61 cubic inch, providing a ratio of surface area to volume of about five. The overall volume of the reservoir is about 1.2 cubic inches, and thus the ratio of surface area of liquid within the reservoir 470 to the overall volume is about two and one half.

The wash cell 448 washes the probe tip 568 by flowing water through the conduit 466 upon operation of the valve 464. Vacuum is simultaneously applied to the lower conduit 446a of the wash cell 454 by operation of the valve 456.

The liquid level detection aspect of the pipette probe 112 is also advantageously used to detect filling of the electrophoresing conduit 284. With the pipette probe 112 at rest in the hole 576 and the probe tip 568 within the wash cell 454, the probe tip 568 acts as a liquid level detector within the wash cell 454. To fill the electrophoresing conduit 284 with running buffer from the reservoir 358, degassed buffer valve 372 and conduit valve 444 are operated, flowing buffer 670 from the reservoir 358 into the electrophoresing conduit 284.

As the electrophoresing conduit 284 is filled, buffer 670 flows through the conduit 442, the open valve 444 and into the wash cell 454 via the conduit portion 446a. When the level of the buffer in the wash cell 454 contacts the probe tip 568, the level sensing circuit 569 provides an output to the controller 610 indicating that buffer is at the predetermined level within the wash cell 454 and that the electrophoresing conduit 284 is thus full. Valves 372 and 444 are then deenergized.

The electrophoresing conduit 284 may also be filled by operating the degassed buffer valve 372 and the conduit valve 444 for a predetermined time.

The operation of the sample handling system 100 in the overall operation of an analyzer may include, for example, the initial preparation of the capillaries 260 after an idle period. Preferably, the capillaries 260 are stored dry. Two empty sample segments 118 are positioned at the holding stations 630, 640, and the pipette probe 112 is moved about by the transfer assembly 104 to pipette sodium hydroxide from one of the reagent containers 664, 666 to, for example, the sample segment 118 at the first holding station 630.

The second empty sample segment 118 is transported by the transport assembly 104 to the coaxial probe assembly and the wells 122 of such sample segment 118 are filled with de-gassed buffer 670. The buffer-filled sample segment 118 is retained at the receiving station 250 and buffer is drawn through the capillaries 260 by application of regulated vacuum applied by operation of the inlet vacuum valve 384. The sodium hydroxide filled sample segment 118 is moved to the receiving station 250 and sodium hydroxide is drawn through the capillaries 260 to clean the inner bores of the capillaries, again by application of regulated vacuum. Finally, buffer is again drawn through the capillaries 260 to clean the sodium hydroxide from the bores and prepare the capillaries 260 for samples.

Samples from the test tubes 116 are transferred to the corresponding sample segment 118 on the sample wheel and the sample-containing sample segment 118 is moved to the receiving station 250. A brief, predetermined application of regulated vacuum draws a correspondingly predetermined volume of samples from the wells 122 into the respective capillaries 260. The sample-containing segment 118 is then returned to the sample wheel, again by the transfer assembly 104, and the buffer-containing segment 118 is moved to the receiving station 250, applying running buffer to the sample ends of the capillaries 250. Electrophoresing voltage is applied via the electrodes 410, 422, separation occurs and the results pass through the optical paths defined by the optical cables 242, producing a detectable result.

The capillaries 250 are again cleaned as described above and additional analytical cycles may be performed.

The present invention is not to be limited to the embodiment disclosed herein, but is to be afforded the full scope of the appended claims and all equivalents thereof.

We claim:

1. A capillary electrophoresis sample handling system suitable for use with a sample segment and a plurality of capillaries, comprising:
an arm including receiving means for receiving and removably retaining the sample segment;
rotational means for moving the arm about a central rotational axis and translational means for moving the arm along a translational axis, the translational axis passing through the rotational axis; and
manifold means for removably receiving the sample segment and the plurality of capillaries.

2. A system as in claim 1 wherein the receiving means includes a port and means for controllably applying a vacuum to the port to thereby removably retain the sample segment by the receiving means.

3. A system as in claim 1 wherein the system includes a frame and the rotational means includes a spindle, bearing means for rotatably retaining the spindle by the frame, the bearing means including a rotational bearing and a resilient member between the rotational bearing and the frame.

4. A system as in claim 3 wherein the resilient member is an o-ring.

5. A system as in claim 4 wherein the rotational bearing has a cylindrical circumference and the o-ring is disposed about the cylindrical circumference, and the frame includes a groove which receives and supports the o-ring.

6. A system as in claim 1 wherein the translational means includes parallel guide shafts having first and second ends, a carriage guided by the guide shafts and which carries the arm, means for moving the carriage along the guide shafts, and means for flexibly mounting the guide shafts at the first end thereof.

7. A system as in claim 6 wherein the means for moving the carriage includes a lead screw having first and second ends proximate the first and second ends of the guide shafts, and the carriage includes a threaded portion engaged with the lead screw, and the system further including a motor means for driving the lead screw, and flexible coupling means connecting the motor means to the lead screw.

8. A system as in claim 1 wherein the system includes a single transport assembly and the transport assembly includes the rotational means and translational means.

9. A capillary electrophoresis sample handling system suitable for use with a plurality of sample segments and a plurality of capillaries, comprising:
a sample wheel for removably receiving and retaining the plurality of sample segments;
a pipette probe;
an arm including receiving means for receiving and removably retaining one of the plurality of sample segments and the pipette probe;
rotational means for moving the arm about a central rotational axis and translational means for moving the arm along a translational axis, the translational axis passing through the rotational axis; and
manifold means for removably receiving the sample segment and the plurality of capillaries.

10. A system as in claim 9 wherein the receiving means includes a port and vacuum means for controllably applying a vacuum to the port to thereby removably retain one of the sample segments or the pipette probe by the receiving means.

11. A system as in claim 10 wherein the system includes support means for supporting the rotational means, and the rotational means includes a spindle, bearing means for rotatably retaining the spindle by the support means, the bearing means including a rotational bearing and a resilient member between the rotational bearing and the support means.

12. A system as in claim 11 wherein the rotational bearing has a cylindrical circumference and the resilient member is disposed about the cylindrical circumference, and the support means includes a groove which receives and supports the resilient member.

13. A system as in claim 10 wherein the rotational means includes motor means for rotating the rotational means and the system further includes control means for controlling the motor means and the vacuum means for retrieving and retaining one of the plurality of sample segments by the arm receiving means and agitating the retrieved and retained sample segment.

14. A system as in claim 9 wherein the pipette probe has a tip, the manifold means has a wash cell, and the system includes means for supporting the pipette probe such that the tip is in the wash cell.

15. A system as in claim 14 wherein the system includes liquid level sensing means for sensing contact between the probe tip and liquid, and the manifold means includes a first conduit and means for receiving an end of capillaries in the conduit, a second conduit providing fluid communication between the first conduit and the wash cell, and valve means for controllably flowing liquid into the first conduit, the liquid level sensing means sensing liquid in the first and second conduits.

16. A system as in claim 9 wherein the sample wheel is adapted to receive a plurality of sample segments at sample segment supports, each of the supports including a slot between the support and an outer edge of the sample wheel, the supports and associated slots being sized to receive the arm.

17. A system as in claim 9 wherein the system includes a single transport assembly and the transport assembly includes the rotational means and translational means.

18. A capillary electrophoresis sample handling system suitable for use with a plurality of sample segments and a plurality of capillaries, comprising:
- a sample wheel for removably receiving and retaining the plurality of sample segments;
- a pipette probe;
- not more than one transport assembly, the transport assembly including an arm having receiving means for receiving and removably retaining one of the plurality of sample segments and the pipette probe, rotational means for moving the arm about a central rotational axis, and translational means for moving the arm along a translational axis, the translational axis passing through the rotational axis; and
- manifold means for removably receiving the sample segment and the plurality of capillaries.

19. A transfer assembly for use in an automated analyzer and useful with sample segments, the transfer assembly including:
- a spindle including at least one guide shaft and a lead screw having threads;
- a carriage carried by the guide shaft and engaged by the threads of the lead screw;
- an arm having a first end fixed to the carriage, and a second end, the second end including receiving means for receiving the sample segments, the receiving means including vacuum and retaining means; and
- motor means coupled to the lead screw for rotating the lead screw and coupled to the spindle for rotating the spindle, carriage and arm.

20. A transfer assembly as in claim 19 wherein the vacuum retaining means includes a resilient boot adapted to receive and seal against the sample segment.

21. A transfer assembly as in claim 20 wherein the resilient boot includes an opening and a sealing rib about the opening for sealing against the sample segment.

22. A transfer assembly as in claim 20 wherein the resilient boot includes an opening and an interior wall shaped to form a seal against the sample segment.

23. A transfer assembly for use in an automated analyzer and useful with sample segments, the transfer assembly including:
- a spindle including at least one guide shaft having an end, a lead screw having threads, and resilient mounting means between the guide shaft end and the spindle;
- a carriage carried by the guide shaft and engaged by the threads of the lead screw;
- an arm having a first end fixed to the carriage, and a second end, the second end including receiving means for receiving the sample segments; and
- motor means coupled to the lead screw for rotating the lead screw and coupled to the spindle for rotating the spindle, carriage and arm.

24. A transfer assembly as in claim 23 wherein the resilient mounting means includes an o-ring disposed about the end and carried by a groove formed in the spindle.

25. A transfer assembly for use in an automated analyzer and useful with sample segments wherein the sample segments include a plurality of wells and at least two of the wells have an exterior surface, the transfer assembly including:
- a spindle including at least one guide shaft and a lead screw having threads;
- a carriage carried by the guide shaft and engaged by the threads of the lead screw;
- an arm having a first end fixed to the carriage, and a second end, the second end including resilient boots having an interior adapted to receive the exterior surface of the at least two wells;
- vacuum means for providing a controlled vacuum to the interior of the resilient boots; and
- motor means coupled to the lead screw for rotating the lead screw and coupled to the spindle for rotating the spindle, carriage and arm.

26. A transfer assembly for use in an automated analyzer and useful with sample segments wherein the sample segments include a plurality of wells and at least two of the wells have an exterior surface, the transfer assembly including:
- a spindle including at least one guide shaft having an end, resilient mounting means between the one end of the guide shaft and the spindle, and a lead screw having threads;
- a carriage carried by the guide shaft and engaged by the threads of the lead screw;
- an arm having a first end fixed to the carriage, and a second end, the second end including resilient boots having an interior adapted to receive the exterior surface of the at least two wells;
- vacuum means for providing a controlled vacuum to the interior of the resilient boots; and
- motor means coupled to the lead screw for rotating the lead screw and coupled to the spindle for rotating the spindle, carriage and arm.

27. A transfer assembly as in claim 26 wherein the resilient mounting means includes an o-ring disposed about the guide shaft end and carried by a groove formed in the spindle.

28. A manifold for use in an automated analyzer and useful with a plurality of capillary assemblies, including:
- a manifold body;
- means for removably retaining the capillary assemblies;
- at least one reservoir formed in the body, the reservoir having a first dimension, a second dimension, and a third dimension, the first and second dimensions being greater than the third dimension, the third dimension being between first and second ends of the reservoir; and
- first, second and third conduits in communication with the reservoir, the first and second conduits in communication with the reservoir being proximate the first end of the reservoir, and the third conduit in communication with the reservoir being proximate the second end thereof.

29. A manifold as in claim 28 wherein the manifold includes an electrophoresing conduit adapted to be in communication with ends of the capillary assemblies, the electrophoresing conduit retaining an electrode.

30. A manifold as in claim 29 wherein the electrode is from sheet stock.

31. A manifold as in claim 30 wherein the sheet stock is stainless steel about 0.004 inch thick.

32. A manifold as in claim 29 wherein the manifold body is unitary.

33. A manifold as in claim 28 wherein the cross section area of the reservoir, defined by product of the first and second dimensions, is substantially greater than the volume of the reservoir, defined by product of the first, second and third dimensions.

34. A manifold as in claim 33 wherein the ratio of the cross section area to the volume is between about two and three.

35. A manifold as in claim 28 wherein the manifold includes means for controllably providing liquid to the first conduit, means for controllably providing vacuum to the second conduit, and means for drawing liquid from the third conduit.

36. A method of using the manifold of claim 35, including the steps of providing liquid to the reservoir until the reservoir is about half full between the first and second ends, providing vacuum to the reservoir for a predetermined time period, and drawing liquid from the reservoir.

37. The method of claim 36 wherein the steps are performed in the order of providing the liquid to the reservoir, providing vacuum to the reservoir, and drawing liquid from the reservoir.

38. A method as in claim 37 wherein the steps are performed separately in time and do not overlap in time.

39. A manifold for use in an automated analyzer and useful with a plurality of capillary assemblies, including
a manifold body having at least first and second conduits;
means for removably retaining the capillary assemblies;
at least one valve having a control element;
a valve adapter disposed between the valve and the manifold, the valve adapter providing communication from the valve control element to the first and second conduits, the valve adapter having a body and being removably fixed to the valve via a neck portion extending from the body; and
a retainer ring including a threaded portion adapted to engage the manifold body and including a surface for engaging the valve adapter body to thereby retain the valve adapter body on the manifold body.

40. A manifold as in claim 39 wherein the neck portion includes a reduced annular portion adapted to fail under stress before the retainer ring threaded portions fails.

41. A manifold for use in an automated analyzer and useful with a plurality of capillary assemblies and a sample segment, the manifold including:
a manifold body;
means for removably retaining the capillary assemblies;
a sample segment receiving station, including a pivoted arm, a solenoid operatively connected to the pivoted arm, and a pressure pad at one end of the arm, the pressure pad being adapted to press against and hold a sample segment against the manifold.

42. A manifold for use in an automated analyzer and useful with a plurality of capillary assemblies and a sample segment, including:
a manifold body;
means for removably retaining the capillary assemblies;
at least one reservoir formed in the body, the reservoir having a first dimension, a second dimension, and a third dimension, the first and second dimensions being greater than the third dimension, the third dimension being between first and second ends of the reservoir;
first, second and third conduits in communication with the reservoir, the first and second conduits in communication with the reservoir being proximate the first end of the reservoir, and the third conduit in communication with the reservoir being proximate the second end thereof;
a sample segment receiving station, including a pivoted arm, a solenoid operatively connected to the pivoted arm, and a pressure pad at one end of the arm, the pressure pad being adapted to press against and hold a sample segment against the manifold;
a liquid dispensing probe;
conduit means between the reservoir and the liquid dispensing probe; and
valve means operatively disposed in the conduit means for controlling the flow of liquid from the reservoir to the liquid dispensing probe.

43. A manifold as in claim 42 wherein the manifold further includes a second probe coaxially disposed with respect to the liquid dispensing probe, and means for applying a controlled vacuum to the second probe.

* * * * *